United States Patent [19]
Jansen et al.

[11] Patent Number: 4,767,621
[45] Date of Patent: Aug. 30, 1988

[54] DRUGS COMPRISING IN ASSOCIATION AT LEAST ONE IMMUNOTOXIN AND AT LEAST ONE MONOVALENT CARBOXYLIC IONOPHORE

[75] Inventors: Franz Jansen, Assas; Pierre Gros, Montpellier, both of France

[73] Assignee: Sanofi, Paris, France

[21] Appl. No.: 650,570

[22] Filed: Sep. 14, 1984

Related U.S. Application Data

[63] Continuation of Ser. No. 548,854, filed as PCT FR83/00025 on Feb. 4, 1983, published as WO83/02725 on Aug. 18, 1983, abandoned.

[30] Foreign Application Priority Data

Sep. 2, 1982 [FR] France .................................. 82 02091

[51] Int. Cl.$^4$ ........................ A61K 39/00; C07K 13/00
[52] U.S. Cl. ...................................... 424/85; 530/387; 530/388; 530/389; 530/390; 530/391; 530/828; 514/6; 514/8
[58] Field of Search .................. 424/85; 530/300, 324, 530/370, 387, 388, 345, 390, 391, 828; 514/2, 8, 12

[56] References Cited

PUBLICATIONS

Biswajit Ray et al, *Chemical Abstracts*, V. 95, No. 36779m, "Enhanced Internalization ... Ovary Cells".
Biswajit Ray et al, *Chemical Abstracts*, V. 95, No. 75056t, "Enhancement of Cytotoxicities ... Nigericin".
Ray et al, *Mol Cell Biol*, vol. 1(6), pp. 552–559, "Enhancement of Cytotoxicities of Ricin and *Pseudomonas* Toxin in Chinese Hamster Ovary Cells by Nigericin".
Ray et al, *Mol Cell Biol*, vol. 1(6), pp. 560–567, "Enhanced Internalization of Ricin in Nigericin-Pretreated Chinese Hamster Ovary Cells".
Alonso et al, *FEBS Lett.*, vol. 127(1), pp. 112–114, 1981, "Permeabilization of Mammalian Cells to Proteins by the Ionophore Nigericin".
Moolten et al, *Immunol Rev.*, vol. 62, pp. 47–73.
Sandvig et al, *J Biol Chem*, vol. 257, pp. 7504–7513.
Jansen et al, *Immunol Rev*, vol. 62, pp. 185–216.

Primary Examiner—Thomas G. Wiseman
Assistant Examiner—Robin Lyn Teskin
Attorney, Agent, or Firm—Stevens, Davis, Miller & Mosher

[57] ABSTRACT

The present invention relates to drugs characterized in that they comprise, in association, at least one immunotoxin and at least one monovalent carboxylic ionophore.

2 Claims, 4 Drawing Sheets

DRUGS COMPRISING IN ASSOCIATION AT LEAST ONE IMMUNOTOXIN AND AT LEAST ONE MONOVALENT CARBOXYLIC IONOPHORE

This application is a continuation of application Ser. No. 548,854, filed as PCT FR83/00025 on Feb. 4, 1983, published as WO83/02725 on Aug. 18, 1983, abandoned.

The present invention relates to novel medicaments comprising in association at least one immunotoxin and at least one monovalent carboxylic ionophore.

In prior French patent applications, bearing particularly numbers: 78 27 838, 79 24 655, 81 07 596 and 81 21 836, there are described the preparation of so-called conjugated anti-cancerous products obtained by coupling, by covalent bonding, the A chain of ricin with antibodies or antibody fragments directed against an antigen borne by a cell to be destroyed. Products of this type are denoted in the present application by the general name of immunotoxins.

As set forth in French Patent No. 78 27838 chain A of ricin/antibody conjugates are prepared by associating by means of a covalent bond of the disulphide type, on the one hand, an immunoglobulin which is specific for a given antigen, or any fragment of this molecule which possesses the capacity of specific recognition with respect to the antigen, with, on the other hand, the A chain of ricin. The choice of a disulphide bond between the A chain and the immunoglobulin is based on the following arguments:

this type of bond is the type which exists in the natural ricin molecule, and it can be expected to be particularly suitable for presenting the A chain in a conformation which facilitates its penetration into the cell, whilst at best retaining its fundamental biological property of inhibiting protein synthesis, this type of bond is biochemically labile, which provides the A chain, coupled in this way, with the possibility of being liberated, from its carrier protein, in the contents of the cell, the A chain of ricin possesses a single cysteine residue in its structure and hence only one SH group capable of creating a disulphide bond. Consequently, the conjugates formed by involving this SH group in a disulphide bridge will be chemically well defined and will in no way modify the structure of the A chain, thus ensuring the integral retention of its biological activity, and there are efficient methods which make it possible to produce such a disulphide bond under conditions which are sufficiently mild to ensure the integrity of the biological properties of the protein constituents of the conjugates formed.

In order to produce such conjugates, the proteins to be coupled must each carry at least one sulphur atom which is naturally capable, or is artificially rendered capable, of creating the desired disulphide bond, whether these sulphur atoms already exist in the proteins or have been chemcially introduced into these proteins. As indicated above, the A chain of ricin naturally possesses only one sulphur atom permitting the desired coupling. This is the sulphur atom in the thiol group of the single cysteine residue incorporated in the A chain. As regards the immunoglobulin or its fragments, several cases must be considered:

(1) In the case of an entire immunoglobulin, neither a free thiol group nor other sulphur atoms capable of being used for the coupling exist naturally in these proteins. It will therefore be necessary, in this case, to introduce one or more sulphur atoms into the immunoglobulin molecule artificially so that:

the biological properties of the immunoglobulin are not profoundly impaired, and this sulphur atom, or these sulphur atoms, can subsequently be involved in the disulphide bond to be established with one or more molecules of the A chain of ricin.

(2) In the case of a Fab fragment, the situation is absolutely identical to that described above.

(3) If a fragment of the Fab' type is employed, it is possible to use the sulphur atom present in the free thiol group to carry out the coupling to the A chain. However, it is also possible to use the artificial introduction of one or more sulphur atoms; in this case, it is necessary to block the free thiol group in a stable manner beforehand, for example by alkylation.

(4) Finally, if it is desired to couple a F(ab')$_2$ fragment of immunoglobulin, it is necessary, as in the case of the whole immunoglobulin, to introduce one or more sulphur-containing groups into F(ab')$_2$ artificially.

In all the cases in which one or more sulphur-containing radicals are introduced into the immunoglobulin or its fragments, it is necessary to avoid any substitution in the site for recognition of the antigen or in its immediate environment, which substitution could disturb the recognition properties of the antibody. In order to exclude this risk, the site for recognition of the antigen can be blocked temporarily, during the substitution reaction, by treating the antibody beforehand with the specific antigen, or with another antigen which possesses an adequate cross-reaction, or with a suitable hapten.

The operation for temporary protection can be carried out:

either in the liquid phase, if the antibody-antigen (or hapten) complex is soluble in the reaction medium, or in the heterogeneous phase, if this complex is spontaneously insoluble or also if it has been deliberately rendered insoluble by means of a suitable procedure, in particular by fixing the antigen (or hapten) to an insoluble support so that the modified support thus obtained possesses an adequate affinity for the antibody.

After the substitution step, it will be necessary to unblock the site for recognition of the antigen, on the antibody, by means of a suitable procedure for removing the antigen, in order to regenerate the capacity of the antibody for specific recognition.

To produce the disulphide bridge between the two proteins, it is not possible to bring the two constituents of the conjugate, each carrying a SH group, into contact with one another and to carry out an oxidation. In fact, under these conditions, the coupling reaction is an equilibrium reaction which is very difficult to drive to completion. Furthermore, the desired reaction is accompanied by the formation of polymers of each of the two constituents, which would result in a very low yield of the desired product and the presence of impurities which are very difficult to remove.

According to the invention, the conjugate is prepared by bringing one of the proteins, carrying its free SH group, into contact with the other protein, in which the SH group is activated by conversion into a mixed disulphide with a suitable sulphur-containing organic radical. The preparation of the conjugate can be represented by the equation:

$$P_1-SH+P_2-S-S-X \rightarrow P_1-S-S-P_2+XSH$$

in which $P_1$ and $P_2$ represent the two proteins to be coupled and X denotes the activator radical. It is immediately apparent from this equation that, in each case, the coupling reaction can be carried out in accordance with two variants, depending on whether $P_1$ represents the immunoglobulin or its fragment and $P_2$ represents the A chain of ricin, or vice versa.

Case in which $P_1$ represents the antibody or a fragment and $P_2$ represents the A chain of ricin To activate the free SH in the A chain of ricin, the solution of A chain, prepared as indicated above, is used, and it is subjected to an exchange reaction:

$$ASH+XSSX \rightarrow A-S-S-X+XSH \qquad (1)$$

in which ASH represents the A chain of ricin and X represents the activator radical.

In particular, X can denote a pyrid-2- or -4-yl group which is optionally substituted by one or more alkyl or halogen radicals or carboxylic acid groups, or X can also represent a phenyl nucleus which is optionally substituted by one or more nitro or carboxylic acid groups. Reaction (1) is an equilibrium reaction but the equilibrium can easily be displaced towards the right by using a large molar excess of the reagent XSSX, which is generally inexpensive and readily accessible. It is possible to monitor the course of reaction (1) by ultraviolet or visible spectrophotometry because the compound XSH which is formed shows an intense absorption in this region. When the reaction has reached the desired degree of completion, the excess of the reagent X—S—S—X, and also the reaction product X—SH, are removed by dialysis or filtration on a molecular sieve in gel form. Finally, a pure solution of the compound A—S—S—X in the chosen buffer is obtained. If necessary, this solution can be kept for several weeks after freezing.

The immunoglobulin substituted by a SH group is also prepared. To do this, the solution of immunoglobulin obtained above is used either as such or after blocking its site for the recognition of the antigen, with the corresponding hapten, followed by removal of the excess hapten. By reacting S-acetylmercaptosuccinic anhydride with this protein, it is possible to fix one or more S-acetylmercaptosuccinyl groups, per molecule of protein, by means of its free amino groups, and then to liberate the thiol groups by the action of hydroxylamine, as has been described [Archives of Biochemistry and Biophysics 119, 41-49 (1967)]. Dialysis makes it possible to remove the excess reagents and also the reaction products of low molecular weight.

All these operations are carried out in a phosphate buffer at pH=7.0 and at temperatures which do not exceed ambient temperature. The hapten which may have been used as a temporary blocking agent is removed from the solution finally obtained. If it proves necessary, this solution can be concentrated, for example by ultrafiltration. The coupling between the two reagents thus prepared is effected by simple contact in aqueous solution, at ambient temperature, for a time varying from a few hours to one day, in accordance with the equation:

$$\text{Prot NH}-CO-\underset{\underset{COO^\ominus}{\overset{|}{CH_2}}}{\overset{|}{CH}}-SH + A-S-S-X \qquad (4)$$

$$\text{Prot NHCO } \underset{\underset{COO^\ominus}{\overset{|}{CH_2}}}{\overset{|}{CH}}-S-S-A + XSH$$

The course of the reaction is followed by spectrophotometric determination of the compound XSH formed. The latter is removed by dialysis and a solution of the expected conjugate is obtained which must be further purified. In fact, it is essential, in particular, to remove the molecules of A—S—S—X which have not reacted and which, if they were present in the conjugate, could give rise to a non-selective toxicity.

The purification can be effected by various known methods such as fractional precipitation with the aid of water-miscible organic solvents or of salts, gel permeation chromatography, or also affinity chromatography on a column formed by an insoluble support on which the antigen (or the hapten) is fixed, against which antigen the antibody employed in the preparation of the conjugate is directed.

These purification methods can be applied directly to the dialysed solution originating from the coupling step. However, better results are obtained, and, in particular, the subsequent formation of polymers of the conjugate is avoided, by the prior blocking of the SH groups which remain free, with a reagent such as N-ethylmaleimide.

Case in which $P_1$ represents the A chain of ricin and $P_2$ represents the antibody In this case, the products required for the coupling are the A chain of ricin and the immunoglobulin (or its fragment), which is substituted by a group carrying one or more activated sulphur atoms. The A chain of ricin is used as obtained by the purification procedure described. The immunoglobulin substituted by an activated sulphur atom is prepared from the immunoglobulin itself by substitution with the aid of a reagent which itself carries an activated sulphur atom, in accordance with the equation:

$$\text{Prot}+Y-R-S-S-X \rightarrow \text{Prot}-R-SS-X$$

in which Prot denotes the immunoglobulin, Y represents a group permitting the covalent fixation of the reagent to the protein, R denotes a group which can simultaneously carry the substituents Y and —S—SX, and X denotes the activator radical.

A reaction of this type has already been used for coupling two proteins (identical or different) by means of a disulphide bridge, but the application of this principle to the coupling of an immunoglobulin with the A chain of ricin is new.

The functional group Y is a group which is capable of bonding in a covalent manner with any one of the groups carried by the side chains of the constituent aminoacids of the protein to be substituted. Amongst these later groups, the terminal amino groups of lysyl radicals, which are present in the protein, are particularly indicated. In this case, Y can represent, in particular:

a carboxylic acid group which can bond to the amino groups of the protein in the presence of a coupling agent such as a carbodiimide and, in particular, a water-soluble derivative such as 1-ethyl-3-(3-diethylaminopropyl)-carbodiimide, a carboxylic acid chloride which is capable of reacting directly with the amino groups in order to acylate them, a so-called "activated" ester, such as an orthoor para-, nitro- or dinitro-phenyl ester or also a N-hydroxysuccinimide ester, which reacts directly with the amino groups in order to acylate them, an internal anhydride of a dicarboxylic acid, such as, for example, succinic anhydride, which reacts spontaneously with the amino groups in order to create amide bonds, or an iminoester group in which $R_1$ is an alkyl group which reacts with the amino groups of the protein in accordance with the equation:

X denotes functional group which is capable of reacting with a free thiol radical.

In particular, X can denote a pyrid-2-yl or pyrid-4-yl group which is optionally substituted by one or more alkyl, halogen or carboxylic acid radicals. X can also denote a phenyl group which is preferably substituted by one or more nitro or carboxylic acid groups. X can also represent an alkoxycarbonyl group such as the methoxycarbonyl group.

The radical R denotes any radical which is capable of simultaneously carrying the substituents Y and S—S—X. The radical chosen must not contain groups which are capable of interfering, in the course of the subsequent reactions, with the reagents used and the products synthesized. In particular, the group R can be a group $-(CH_2)_n$, in which n is between 2 and 10, or also a group in which $R_4$ denotes hydrogen or an alkyl group having from 1 to 8 carbon atoms, and $R_3$ denotes a substituent which is inert towards the reagents subsequently used, such as an amide group in which $R_5$ denotes a linear or branched alkyl group having from 1 to 5 carbon atoms, in particular the tert.-butyl group.

The reaction of the compound Y—R—S—S—X with the immunoglobulin is carried out in the homogeneous liquid phase, most frequently in water or a buffer solution. When required by the solubility of the reagents, it is possible to add, to the reaction medium, up to 20% by volume of a water-miscible organic solvent such as an alcohol, in particular tertiary butanol.

The reaction is carried out at ambient temperature for a time which varies from a few hours to 24 hours. Thereafter, dialysis makes it possible to remove the products of low molecular weight and, in particular, the excess reagents. This process makes it possible to introduce a number of substituent groups of between 1 and 5 per molecule of protein.

Using such compounds, the coupling with the A chain of ricin is carried out by bringing the two proteins into contact with one another in aqueous solution, at a temperature which does not exceed 30° C., for a time which varies from a few hours to one day. The reaction takes place in accordance with the equation:

in which Prot—R—S—S—X represents the substituted immunoglobulin (or its fragment), activated on the sulphur atom, and ASH represents the A chain of ricin. The solution obtained is dialysed in order to remove the products of low molecular weight, and the conjugate can then be purified by various known methods, as indicated in the first process for the preparation of the conjugates.

In French application 81/21 836, there is described, in addition, the property of ammonium ions (in the form of any one of their salts and in particular the chloride) to potentiate effectively the cytotoxic action of these immunotoxins.

The property of ammonium salts to potentiate the selective cytotoxic activity of immunotoxins has numerous advantages in two types of situations.

(a) Each time that an immunotoxin is used as a selective cytotoxic agent in vitro to destroy the target cells.

In the case of therapeutic applications, this situation is encountered particularly when the immunotoxin is used as a cytotoxic agent in the treatment of bone marrow of leucemic patients in whom the bone marrow thus treated will be subsequently transplanted, as has been described in the patent application filed in France under number 81/21 836 by applicant.

(b) When the immunotoxin is used in vivo as therapeutic agent in man each time that it is possible to administer preventively, simultaneously or subsequently to the patient an ammonium salt ensuring the potentiation of the immunotoxin effect, as has been described in the above-mentioned patent application.

However, in the latter case of in vivo use of the immunotoxin, the employment, also in vivo, of an ammonium salts in order to benefit from the potentiating effect experiences certain limitations inherent in the toxicity itself of the ammonium ions and in fact it is relatively inconvenient to maintain durably a sufficient concentration of ammonium ions in the biological fluids of the patient.

An object of the present invention is the preparation of powerful cytotoxic medicaments using the potentiation of the selective cytotoxic effects of the immunotoxins described in the previously mentioned prior applications.

After numerous substances had been studied without success, it was found that the monovalent carboxylic ionophore represented a group of particularly interesting substances to potentiate the cytotoxic effect of immunotoxins.

By carboxylic ionophore, is meant natural substances isolated from Streptomyces strains which include a hydrocarbon linear skeleton in which are included oxygen heterocyclic rings. At one end of the chain, there still exists a carboxylic acid function whilst at the other end occur one or several alcohol functions [see B.C. Pressman : Annual Review of Biochemistry 45, 501–530, (1976)].

These products have the property of forming liposoluble complexes with numerous cations enabling these ions to pass through the lipid barriers. Those which form such complexes with monovalent cations constitute the family of monovalent carboxylic ionophore of which the best known representatives are: monensin, nigericin, grisorixin and lasalocide.

These monovalent carboxylic ionophore possess various biological properties and particularly antibiotic and antiparasitic properties. Also, for example, monensin is used as an adjuvant in the feeding of cattle and as a coccidiostatic agent in poultry.

It has been also indicated [B. Ray and H. C. Wu, Molecular and Cellular Biology 1, 552–559, (1981)] that monensin and nigericin increase the cytotoxicity of ricine with respect to certain cell lines. This increase is however modest of the order of factor 10.

In the present invention, it has been found that, surprisingly, monovalent carboxylic ionophore used at doses where they do not themselves have any cytotoxicity itself for the lines studied potentiate to an extremely great degree (factors of 7 000–55 000) the specific cytotoxicity of immunotoxins.

The following non-limiting example enables the scope of the invention to be better understood.

EXAMPLE

This example demonstrates the potentiation of the selective cytotoxicity of the immunotoxin anti-T-65 (described in application number 81/21836 of applicant) with respect to human T lymphoblastoid cells of the CEM line bearing the antigen T-65.

As described in French patent application number 81/21836, the conjugate obtained by reaction between a human anti-cell T antibody (antibody directed against the antigen T65) substituted by an activated disulfide group and a chain A of ricin is prepared as follows:

Human anti-cell T antibody (or antibody T101) was obtained according to the method described in the Journal of Immunology 123 (2), 725–737 (1980). It undergoes ultimate purification by dialysis against a PBS buffer (10 mM of phosphate, 140 mM of sodium chloride, pH 7.4).

Activated human anti-cell T antibody was prepared as follows:

To 0.5 ml of a solution of 14.2 mg/ml of 3-(2-pyridyl disulfanyl) propionic acid in tertiobutanol is added 0.1 ml of a solution of 42.7 mg/ml of 1-ethyl 3-(3-dimethylamino propyl) carbodiimide and the solution is left for 3 minutes at ambient temperature. 180 μl of the solution thus obtained are added to 5.6 ml of a solution of anitbody at 3.6 mg/ml in the PBS buffer. Incubation is allowed to continue for 20 hours at 30° C. The solution is then continuously dialysed for 3 days against 21 liters of PBS buffer at 4° C. 16 mg of activated antibody are thus obtained at a concentration of 2.6 mg/ml. By spectrophotometric assay at 343 nm of the pyridine 2-thione released by exchange with the reduced glutathion, it is observed that an anitbody carrying 3.1 activator groups per mole of antibody is obtained.

The conjugate was prepared by adding to 4.6 ml of a solution of activated antibody in the PBS buffer (concentration 2.6 mg/ml, or 12 mg of activated antibody) 0.87 ml of a solution of chain A of ricin in the same buffer (concentration 6.6 mg/ml) and incubation is carried out at 25° C. for 20 hours. The reaction mixture is chromatographed over a Sephadex G100 gel column. In each fraction, the concentration in antibody is determined by spectrophotometry at 280 nm and that of the chain A is determined by it power of inhibition of the proteosynthesis measured on an acellular system. The identical fractions containing the conjugate are brought together and about 11 mg of the conjugate at the concentration of 0.8 mg/ml are obtained.

In these experiments, the cytotoxicity has been evaluated by the measurement of the incorporation of 14C-leucine by the cells after 24 h of incubation at 37° C. in the presence of known amounts of the immunotoxins studied, or of reference cyctotoxic substances, in the absence or in the presence of the ionophore to be tested.

1 - Potentiation of the cytotoxic effect by the ionophore

The results of these experiments are presented in the form of dose/effect curves having as ordinate the cytotoxic effect as evaluated as indicated above by the incorporation of the tracer, calculated in % of the value obtained in control cells without cytotoxic substance, and as abscissae the molar concentrations in toxic subunits of the cytotoxic substances studied. Monensin and grisorixin were tested at the concentration of 50 nanomolar, nigericin at the concentration of 10 nanomolar and lasalocide at the concentration of 1 micromolar. It was previously checked that these substances were not spontaneously cytotoxic for the cells employed, at the concentrations indicated.

FIG. 1 shows the effect of monensin on the cytotoxicity itself of ricin (R) and of its isolated chain (A), taken as reference substances. The values of the molar concentrations ($IC_{50}$) corresponding to 50% of inhibition of incorporation of the tracer are indicated in Table 1. The four curves obtained are respevtively relative to: the A chain of ricin (A), a mixture of chain A of ricin and monensin (A)+M, ricin (R) and a mixture of ricin and monensin (R)+M.

TABLE I

| Substances tested | With monensin 50 nM | Without monensin |
|---|---|---|
| Ricin (R) | $4 \cdot 10^{-13}$ M | $2 \cdot 8 \cdot 10^{-12}$ M |
| Chain A (A) | $2 \cdot 7 \cdot 10^{-9}$ M | $1 \cdot 3 \cdot 10^{-7}$ M |

These results demonstrate a certain potentiating effect of monensin on the cytotoxicity of ricin (potentiation factor 7) and of the chain A (potentiation factor 47).

FIGS. 2 and 3 show the comparative potentiating effect of the $NH_4^+$ ion (10 mM), of monensin (50 nM), of nigericine (10 nM), of grisorixin (50 nM) and of lasalocide (1 μM), on the cytotoxicity of the immunotoxin anti-T-65 with respect to the cells of the CEM line. The values of the molar concentrations ($IC_{50}$) corresponding to 50% inhibition of incorporation of the tracer are given in Table II.

Figure 1:
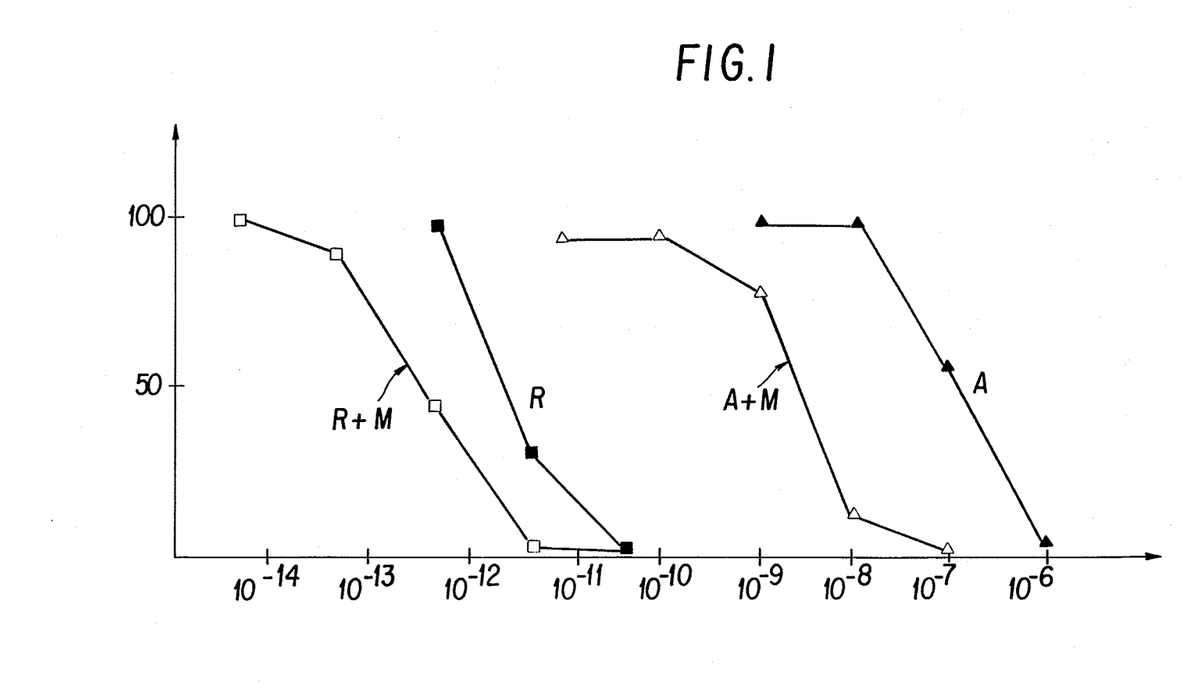
Figure 2:
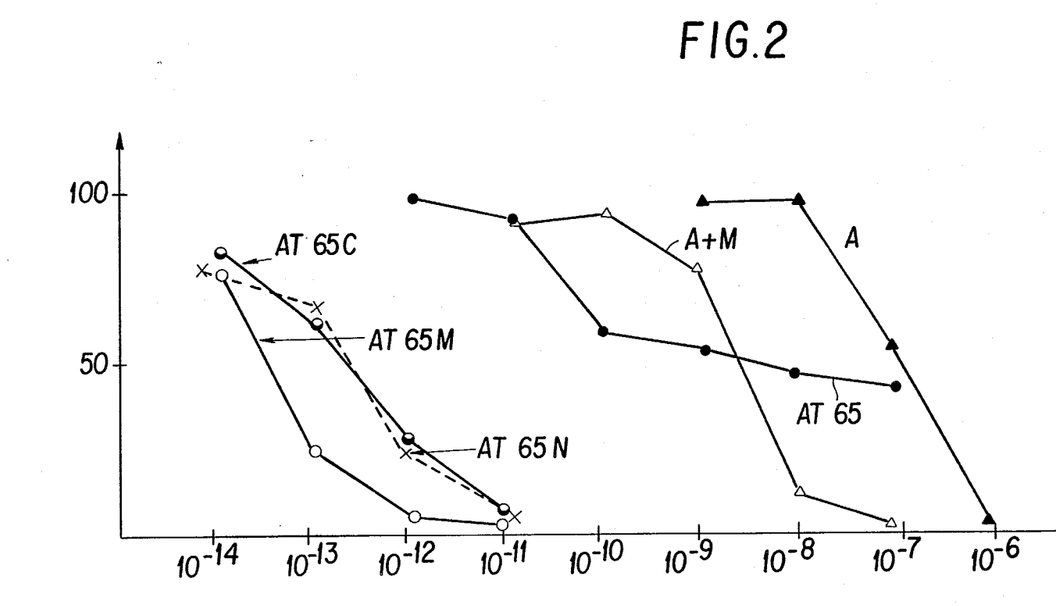
Figure 3:
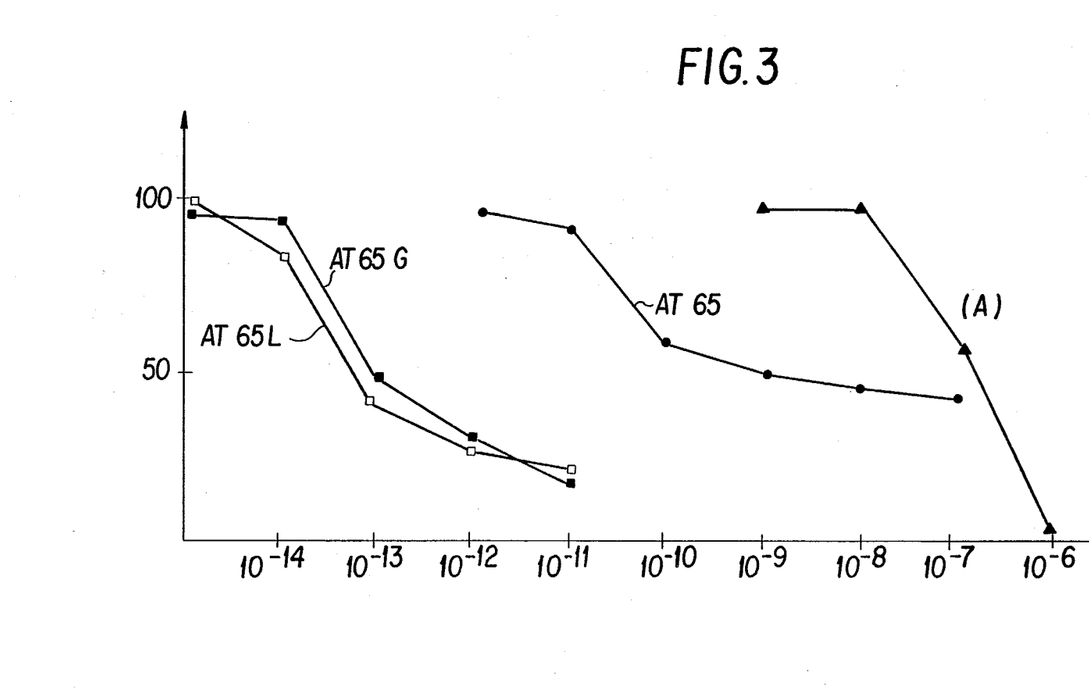

In these figures, the various curves relate respectively to the results obtained with: chain A of ricin (A), chain A of ricin mixed with monensin (A)+(M), the conjugate anti-T-65 (AT65) and the conjugate AT65 supplemented with nigericin (AT65N), monensin (AT65M), ammonium chloride (AT65C), grisorixin (AT65G) and lasalocide (AT65L).

These results show that the potentiating effect of nigericin is very close to that of ammonium ion and of the order of the factor of 7000, whilst that of monensin is distinctly higher, of the order of 55000. Grisorixin and lasalocide occupy an intermediate position with potentiating effects of the order of 27000 and 36000 respectively. These factors are considerably higher than those observed with ricin or the isolated chain A. It must also be noted that in the presence of monensin particularly, immunotoxin anti-T-65 is a cytotoxic agent close to 10 times more powerful that ricin itself, whilst having (contrary to ricin) a remarkable selectivity factor for the target cells alone.

TABLE II

| Potentiating substances tested | $IC_{50}$ |
| --- | --- |
| None | $2 \cdot 2 \cdot 10^{-9}$ M |
| $NH_4^+$ 10 mM | $3 \cdot 10^{-13}$ M |
| Monensin 50 nM | $4 \cdot 10^{-14}$ M |
| Nigericin 10 nM | $3 \cdot 10^{-13}$ M |
| Grisorixin 50 nM | $8 \cdot 10^{-14}$ M |
| Lasalocide 1 μM | $6 \cdot 10^{-14}$ M |

2 - Acceleration of the kinetics of cytotoxicity by ionophore

The effect of the ionophora is not limited to increasing considerably the cytotoxic activity of the immunotoxins. These substances also enable the acceleration very considerably of the kinetics of cytotoxicity of the immunotoxins, as shown by the following experiments:

In these experiments, there were measured as previously, the incorporation of the radio-active tracer in the cells but this time as a function of the incubation time of the cells with the immunotoxin, in the absence and in the presence of 50 nM monensin as potentiator. This experiment was carried out on two cell models by using the immunotoxins of corresponding specificities, namely:

The CEM human hyphoblastoid line with anti-T-65 immunotoxin at the concentration of 50 nM. The results are presented in FIG. 4. In this figure, the curves relate respectively to anti-T-65 (AT65) and the mixture of anti-T-65 and monensin (AT65M). The WEHI 7 mouse lymphoma line with the immunotoxin anti-Thy 1.2 (described in application No. 79 24655 of applicant) at the concentration of 50 nM.

As described in French patent application No. 79/24655, anti-Thy 1.2 IgM antibody is prepared from the ascites liquid obtained from OLAC LTD (Thy 1.2 F7 D5 monoclonal IgM cytoxic antibody). To 50 ml of ascites liquid containing the antibody are added 15 g of powdered ammonium sulphate. After dissolution, the mixture is incubated for one hour at 4° C. and the whole is then centrifugated for 20 minutes at 17,000×g. The supernatant after centrifugation is removed. The deposit is dissolved in 20 ml of 100 mM phosphate buffer, pH=7.0, then the solution is dialysed continuously against 10 liters of the same buffer. The solution obtained is deposited on a column of internal diameter 50 mm containing 1800 ml of Sepharose 6B ® equilibrated with 100 mM phosphate buffer, pH=7.0. Elution is carried out with the same buffer: the first peak obtained corresponds to IgM aggregates. The second peak obtained is collected in two fractions: the first fraction (from the front part to the top of the peak) is constituted by pure IgM; the second fraction contains a mixture of IgM with a contaminating protein of molecular weight estimated at about 660,000 dalton. This second fraction is again treated with ammonium sulphate and the precipitate obtained is centrifugated and re-dissolved in the 100 mM phosphate buffer, pH=7.0. The solution obtained is deposited on the Sepharose 6B ® column suitably washed after the first operation. Elution by the 100 mM phosphate buffer, pH=7.0 gives rise as in the first operation, to the production of two peaks. The second peak obtained contains pure IgM. Each of both filtration operations on Sepharose 6B ® has thus permitted a fraction containing pure IgM to be obtained. These two fractions are brought together and the whole is treated with ammonium sulphate at a final concentration of 300 mg/ml, at 4° C. The preparation is centrifugated for 20 minutes at 17000×g, then the deposit is diluted in the 100 mM phosphate buffer, pH=7.4 and mixed with 400 mM sodium chloride.

Activated anti-Thy 1.2 antibody was prepared by adding to 7.6 ml of the solution of IgM at a concentration of 7.0 mg/ml of a mixture of water/t. butanol 1/5 (V/V) containing 2.9 mg of 1-ethyl-3(3-dimethyl amino propyl) carbodiimide and 7.7 mg of 3(2-pyridyl disulphanyl) propionic acid. The mixture is incubated for 20 hours at 30° C. The solution is then dialysed continuously against the 100 mM phosphate buffer, pH=7.4, mixed with 400 mM sodium chloride and the disodic salt of 1 mM ethylendiaminotetracetic acid. The dialysis is continued for 23 hours at 4° C. at the rate of 500 ml/hour. The solution is subsequently centrifugated at 24,000×g at 4° C. for 10 minutes and the supernatant is recovered. Spectrophotometric determination at 343 nm of the pyridine 2-thione liberated by exchange with the reduced glutathione shows that the activation of the antibody has resulted in the averge substitution rate of 13 activator groups per mol of IgM.

To 6.8 ml of the solution of activated IgM obtained as described above are added 3.9 ml of dialysed ricin A chain, at a concentration of 7.4 mg/ml. The mixture is incubated for 24 hours at ambient temperature in a nitrogen atmosphere and in the absence of light. The determination of the pyridine 2-thione liberated during the reaction indicates that the average coupling rate of 9.7 equivalents of A chain per mol of IgM.

Figure 5:
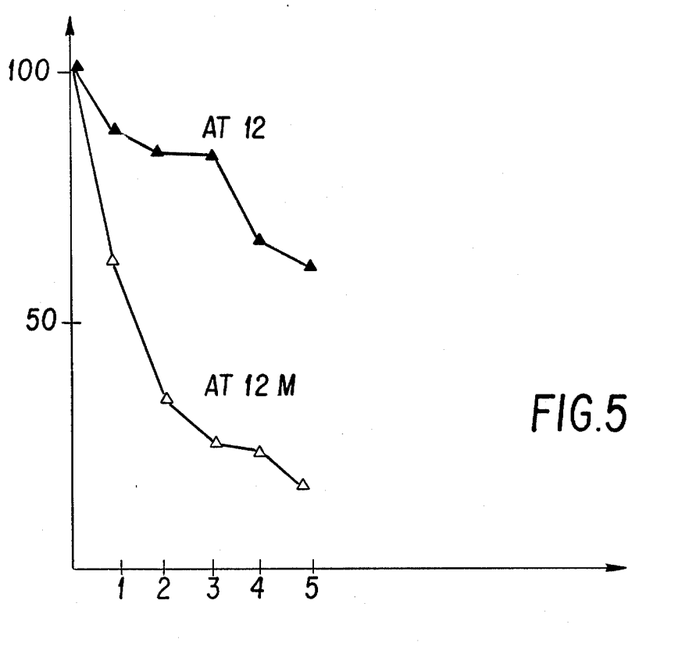

The solution is deposited on a column of internal diameter 50 mm containing 1727 ml of Sepharose 6B ® equilibrated with the conjugation buffer. Elution is conducted with the same buffer. The fractions are collected under a volume of 3.7 ml and the analysis of the fractions is carried out as described in examples 5 and 6 of the parent application. The conjugation product comes out into two peaks: The first corresponds to the conjugate with an average molecular weight higher than that of the IgM. The second peak corresponds to the conjugate with an average molecular weight approximately equivalent to that of the IgM. The central part of this peak (solution i) is retained. The results are presented in FIG. 5. In this figure, the curves relate respectively to the conjugate anti-Thy 1.2 (AT12) and to the mixture of this conjugate with monensin (AT12.M).

Figure 4:
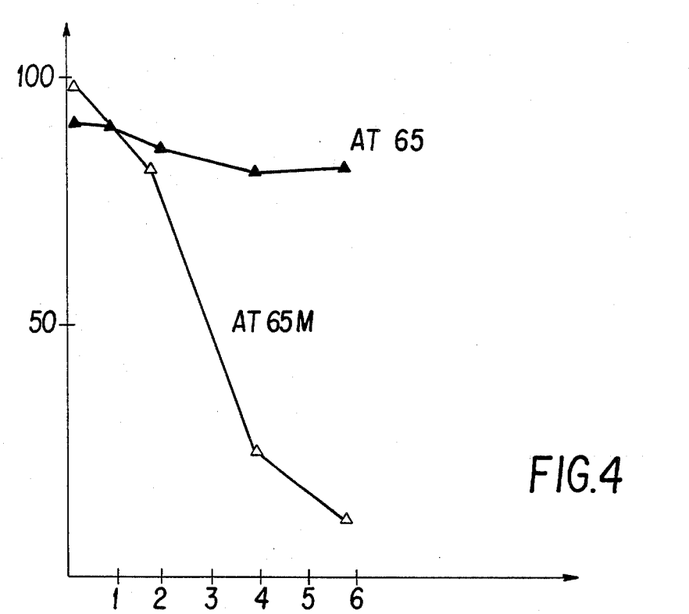

For the CEM line, it appears that, in the absence of potentiation, the cytotoxicity kinetics is very slow as shown by curve a. Other experiments under the same conditions have shown that the time necessary to obtain 50% reduction of the incorporation of the tracer was of the order of 20 hours. On the other hand, in the presence of monensin, a spectacular acceleration of the kinetics was manifested (curve b) since the time necessary to obtain 50% inhibition of incorporation is then of the order of 3 hours only.

For the WEHI 7 line the results are similar since the times necessary to obtain 50% inhibition of incorporation are respectively, in the absence and in the presence of monensin: 10 hours and 1.5 hour.

Such an acceleration effect is of the highest importance for all applications of immunotoxins and in particular for therapeutic applications in vivo since the rapidity of action of the medicament is always a very favorable factor in the effectiveness of the treatment.

In addition, we have studied the toxicity of the monovalent carboxylic ionophore either alone or in association with the A chain of ricin.

According to J. W. Westley [Advances in Applied Microbiology, 22, 177, (1977)], the 50% lethal doses ($LD_{50}$) in the mouse intra-peritoneally are respectively: 16.8 mg/kg for monensin, 65 mg/kg for nigericin, 15 mh/kg for grisorixin, and 64mg/kg for lasalocide.

These results have been confirmed by our own experiments. Thus the acute toxicity of monensin in a single administration intra-peritoneally in the Charles River France mouse is characterised by a 50% lethal dose of 340 micrograms per mouse, namely 17 mg/kg of body weight.

In addition, as it has been shown above that monensin potentiates slightly the cytotoxic activity of the A chain of ricin on cells in culture, it was important to check on this model system of non-specific cytotoxicity, what was the overall toxicological impact of this property on the whole animal. For this, we have determined the 50% lethal dose of the A chain of ricin administered intra-peritoneally in the Charles River France CD1 mouse, in the absence or with coadministration of 10 micrograms or 20 micrograms of monensin per mouse intraperitoneally The values found are the following:

| | |
|---|---|
| $LD_{50}$ Chain A alone | 511 micrograms per mouse |
| $LD_{50}$ Chain A + 10 μg monensin | 363 micrograms per mouse |
| $LD_{50}$ Chain A + 20 μg monensin | 203 micrograms per mouse |

These results show a slight increase in the toxicity of chain A when it is administered at the same time as monensin. This increase of toxicity by a factor of only 2.5 (for the strongest dose of monensin tested) does not constitute a limitation in the use in vivo of the ionophore taking into account the very considerable potentiating and accelerator effects with respect to the specific cytotoxicity of the immunotoxins, as has been shown above.

It is thus possible to use as medicaments in human therapeutics the association constituted by immunotoxin and a monovalent carboxylic ionophore. They may be used for the treatment of diseases, cancerous or not, which would be sensitive to the antibodies used for the preparation of the immunotoxin.

With the object of eliminating all of the cancerous cells, the treatment should be carried out with a sufficient dose of immunotoxin associated with an amount of monovalent carboxylic ionophore which can vary from 1 to 100 mg on each administration of immunotoxin. The duration of the treatment will have to be determined in each case according to the subject and the nature of the disorder to be treated.

The novel medicaments according to the invention are packaged to be used by the injectible route and preferably by the intravenous route.

Preferably the constituents of the association will be preserved separately and mixed, only at the time of use, in the syringe or the perfusion solvent.

We claim:

1. A cytotoxic composition comprising a cytotoxic amount of an immunotoxin and a potentiating amount of a monovalent carboxylic ionophore selected from the group consisting of monensin, nigericin, grisorixin and lasalocide, said immunotoxin comprising the A chain of ricin covalently bonded to an antibody, or antibody fragment directed against an antigen carried by the cells to be destroyed.

2. The cytotoxic composition of claim 1 which is in the form suitable for administration via injection.

* * * * *